US00PP24819P2

(12) United States Plant Patent
Wood

(10) Patent No.: US PP24,819 P2
(45) Date of Patent: Aug. 26, 2014

(54) BARBERRY PLANT NAMED 'HELEN'

(50) Latin Name: *Berberis thunbergii*
Varietal Denomination: Helen

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 175 days.

(21) Appl. No.: 13/507,788

(22) Filed: Jul. 27, 2012

(51) Int. Cl.
*A01H 5/00* (2006.01)

(52) U.S. Cl.
USPC ..... Plt./241

(58) Field of Classification Search
CPC ..... A01H 5/12
USPC ..... Plt./241
See application file for complete search history.

*Primary Examiner* — June Hwu
(74) *Attorney, Agent, or Firm* — C. A. Whealy

(57) ABSTRACT

A new and distinct cultivar of *Barberry* plant named 'Helen', characterized by its upright and outwardly spreading to arching plant habit; vigorous growth habit; freely branching habit; leaves that are dark purple to dark brown in color numerous pale yellow-colored flowers; good garden performance; and resistance to Black Stem Rust.

2 Drawing Sheets

Botanical designation: *Berberis thunbergii.*
Cultivar denomination: 'HELEN'.

BACKGROUND OF THE INVENTION

The present invention relates to a new and distinct cultivar of *Barberry* plant, botanically known as *Berberis thunbergii* and hereinafter referred to by the name 'Helen'.

The new *Barberry* plant is a product of a planned breeding program conducted by the Inventor in Grand Haven, Mich. The objective of the breeding program was to develop new unique *Barberry* plants with attractive foliage, improved stress tolerance and resistance to Black Stem Rust (*Puccinia graminis*).

The new *Barberry* plant originated from an open-pollination in June, 2003 of *Barberry thunbergii* 'Concorde', not patented, as the female, or seed parent and an unknown selection of *Barberry thunbergii* as the male, or pollen, parent. The new *Barberry* plant was discovered and selected by the Inventor during the summer of 2006 as a single plant within the progeny of the stated open-pollination in a controlled environment in Grand Haven, Mich.

Asexual reproduction of the new *Barberry* plant by softwood cuttings in a controlled greenhouse environment in Grand Haven, Mich. since the summer of 2006 has shown that the unique features of this new *Barberry* plant are stable and reproduced true to type in successive generations of asexual reproduction.

SUMMARY OF THE INVENTION

Plants of the new *Barberry* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Helen'. These characteristics in combination distinguish 'Helen' as a new and distinct *Barberry* plant:

1. Upright and outwardly spreading to arching plant habit.
2. Vigorous growth habit.
3. Freely branching habit.
4. Leaves that are dark purple to dark brown in color.
5. Numerous pale yellow-colored flowers.
6. Good garden performance.
7. Resistance to Black Stem Rust.

Plants of the new *Barberry* can be compared to plants of the female parent, 'Concorde'. Plants of the new *Barberry* differ from plants of 'Concorde' in the following characteristics:

1. Plants of the new *Barberry* are larger than plants of 'Concorde'.
2. Plants of the new *Barberry* grow faster than plants of 'Concorde'.
3. Plants of the new *Barberry* have healthier and more durable leaves than plants of 'Concorde'.

Plants of the new *Barberry* can be compared to plants of the *Berberis thunbergii* 'Atropurpurea', not patented. In side-by-side comparisons conducted in Grand Haven, Mich., plants of the new *Barberry* differed from plants of 'Atropurpurea' in the following characteristics:

1. Plants of the new *Barberry* grow more uniformly than plants of 'Atropurpurea'.
2. Leaves of plants of the new *Barberry* were more red in color than leaves of plants of 'Atropurpurea'.
3. Plants of the new *Barberry* were resistant to Black Stem Rust whereas plants of 'Atropurpurea' were not resistant to Black Stem Rust.

Plants of the new *Barberry* can also be compared to plants of the *Berberis thunbergii* 'Rose Glow', not patented. In side-by-side comparisons conducted in Grand Haven, Mich., plants of the new *Barberry* differed primarily from plants of 'Rose Glow' in leaf color as plants of 'Rose Glow' had bright red and pink variegated leaves.

BRIEF DESCRIPTION OF THE PHOTOGRAPHS

The accompanying colored photographs illustrate the overall appearance of the new *Barberry* plant showing the colors as true as it is reasonably possible to obtain in colored reproductions of this type. Colors in the photographs may differ slightly from the color values cited in the detailed botanical description which accurately describe the colors of the new *Barberry* plant.

The photograph on the first sheet is a side perspective view of a typical plant of 'Helen' grown in an outdoor nursery.

The photograph on the second sheet is a close-up view of a typical plant of 'Helen'.

DETAILED BOTANICAL DESCRIPTION

The aforementioned photographs and following observations, measurements and values describe plants grown during the spring and summer in an outdoor nursery in Grand Haven, Mich. and under cultural practices which closely approximate commercial production. Plants used for the photographs were two years old and plants used for the description were four years old. In the following detailed description, color references are made to The Royal Horticultural Society Colour Chart, 1995 Edition, except where general terms of ordinary dictionary significance are used.

Botanical classification: *Berberis thunbergii* 'Helen'.

Parentage:

*Female, or seed, parent.*—*Barberry thunbergii* 'Concorde', not patented.

*Male, or pollen, parent.*—Unknown selection of *Barberry thunbergii*, not patented.

Propagation:

*Type.*—By softwood cuttings.

*Time to initiate roots, summer.*—About 70 days at 20° C.

*Time to produce a rooted young plant, summer.*—About one year at 20° C.

*Root description.*—Fine to medium; somewhat fleshy and fibrous; yellow in color.

*Rooting habit.*—Freely branching; dense.

Plant description:

*Plant form and growth habit.*—Perennial shrub; upright and outwardly spreading to arching plant habit; rapid growth rate and vigorous growth habit; freely branching habit with about 47 lateral branches developing per plant.

*Plant height.*—About 84 cm.

*Plant diameter* (*area of spread*).—About 84 cm.

Lateral branch description:

*Length.*—About 15 cm.

*Diameter.*—About 2 mm.

*Internode length.*—About 1.5 cm.

*Aspect.*—Erect to about 30° from vertical to arching.

*Strength.*—Strong.

*Texture.*—Smooth, glabrous.

*Color.*—Close to 185A.

*Thorns.*—Quantity: About one thorn develops at each node. Length: About 1 cm. Width: About 1 mm. Color: Close to 164A.

Foliage description:

*Arrangement.*—Alternate or whorled; simple.

*Length.*—About 2 cm.

*Width.*—About 1 cm.

*Shape.*—Roughly spatulate.

*Apex.*—Acute, mucronate.

*Base.*—Attenuate.

*Margin.*—Entire.

*Texture, upper and lower surfaces.*—Smooth, glabrous.

*Venation pattern.*—Pinnate.

*Color.*—Developing leaves, upper and lower surfaces: Close to 178B. Fully expanded leaves, upper surface: Between 187A and 200A; venation, close to 187A; plants maintain dark purple to dark brown coloration during the autumn. Fully expanded leaves, lower surface: Close to 187B; venation, close to 187B.

*Petiole.*—Length: About 5 mm. Diameter: About 2 mm. Texture, upper and lower surfaces: Smooth, glabrous. Color, upper and lower surfaces: Close to 187A.

Flower description:

*Flower type and habit.*—Rotate flowers arranged in axillary racemes; flowers drooping; freely flowering habit with about two to six flowers per inflorescence and about ten to 40 flowers per lateral branch.

*Natural flowering season.*—Plants flower continuously from mid to late May in Grand Haven, Mich.

*Flower longevity.*—Flowers last about two to three weeks on the plant; flowers not persistent.

*Fragrance.*—None detected.

*Flower buds.*—Height: About 2 mm. Diameter: About 2 mm. Shape: Globose. Color: Close to 140B.

*Inflorescence height.*—About 1.3 cm.

*Inflorescence width.*—About 1.5 cm.

*Flower diameter.*—About 7 mm.

*Flower depth.*—About 6 mm.

*Petals.*—Quantity per flower and arrangement: Six in a single whorl. Length: About 5 mm. Width: About 4 mm. Shape: Broadly ovate. Apex: Broadly acute to obtuse. Margin: Entire. Texture, upper and lower surfaces: Smooth, glabrous. Color: Developing petals, upper and lower surfaces: Close to 11B. Fully expanded petals, upper and lower surfaces: Close to 11C; color becoming closer to 11D with development.

*Sepals.*—Quantity per flower and arrangement: Six in a single whorl. Length: About 4 mm. Width: About 3 mm. Shape: Ovate. Apex: Broadly acute to obtuse. Base: Obtuse. Margin: Entire. Texture, upper and lower surfaces: Smooth, glabrous. Color: Developing sepals, upper surface: Close to 11B. Developing sepals, lower surface: Close to 11B tinged with close to 60A. Fully expanded sepals, upper surface: Close to 11C. Fully expanded sepals, lower surface: Close to 11C tinged with close to 60C.

*Peduncles.*—Length: About 8 mm. Diameter: About 1.5 mm. Strength: Strong. Color: Close to 60C.

*Pedicels.*—Length: About 4 mm. Diameter: About 1 mm. Strength: Strong. Color: Close to 60C.

*Reproductive organs.*—Stamens: Quantity per flower: Six. Anther shape: Two-valved. Anther length: About 1.5 mm. Anther color: Close to 11A to 11B. Pollen amount: Scarce. Pollen color: Close to 11A to 11B. Pistils: Quantity per flower: One. Pistil length: About 3 mm. Stigma shape: Flattened disc. Stigma color: Close to 143C to 143D. Style length: About 2.5 mm. Style color: Close to 143C to 143D. Ovary color: Close to 143C.

*Seeds and fruits.*—Seed and fruit development has not been observed on plants of the new *Barberry* plant.

Garden performance: Plants of the new *Barberry* have been observed to have excellent garden performance and to tolerate rain, wind and temperatures ranging from about −30° C. to about 32° C.

Pathogen & pest resistance: Plants of the new *Barberry* have been observed to be resistant to Black Stem Rust (*Puccinia graminis*). Plants of the new *Barberry* have not been shown to be resistant to pests and other pathogens common to *Barberry* plants.

It is claimed:

1. A new and distinct *Barberry* plant named 'Helen' as illustrated and described.

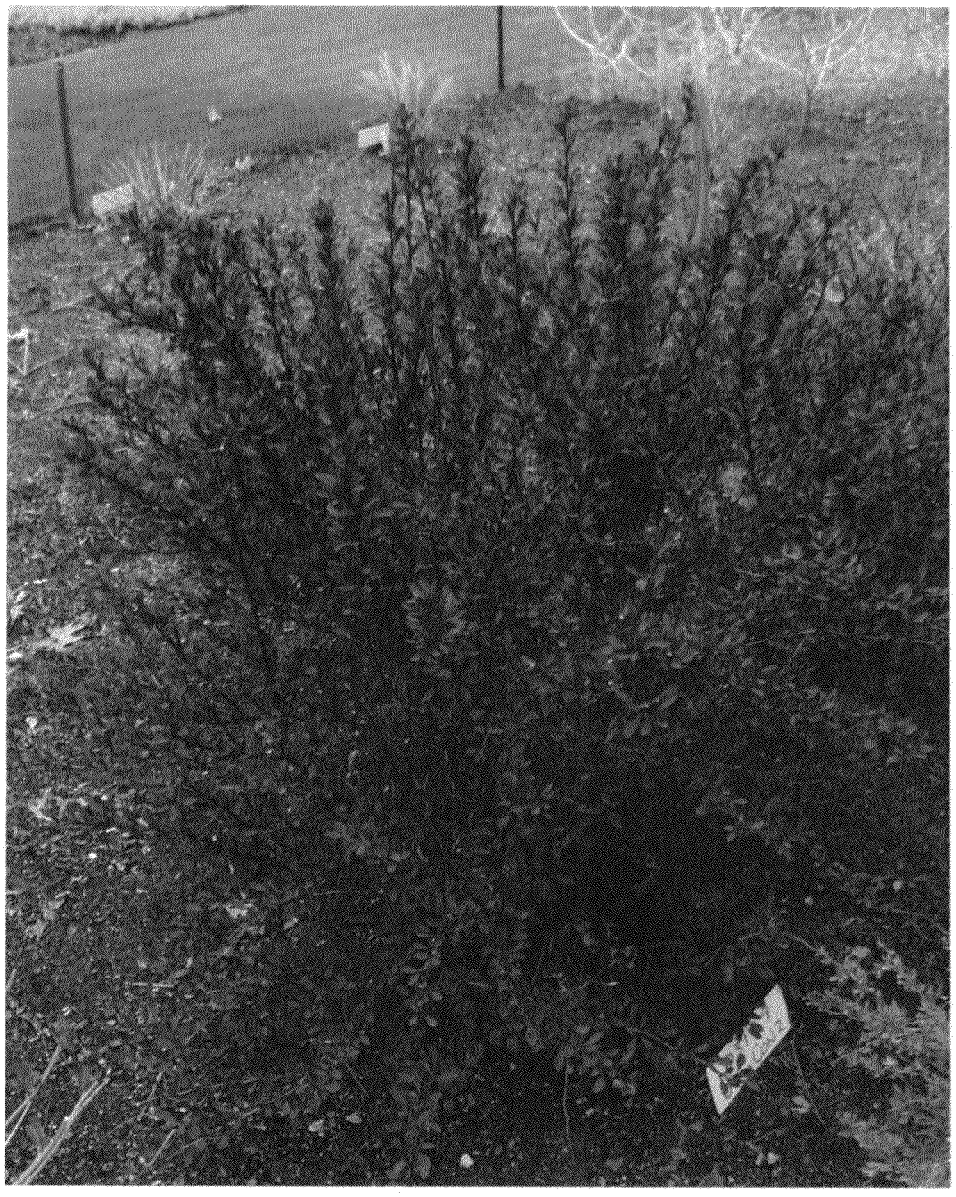

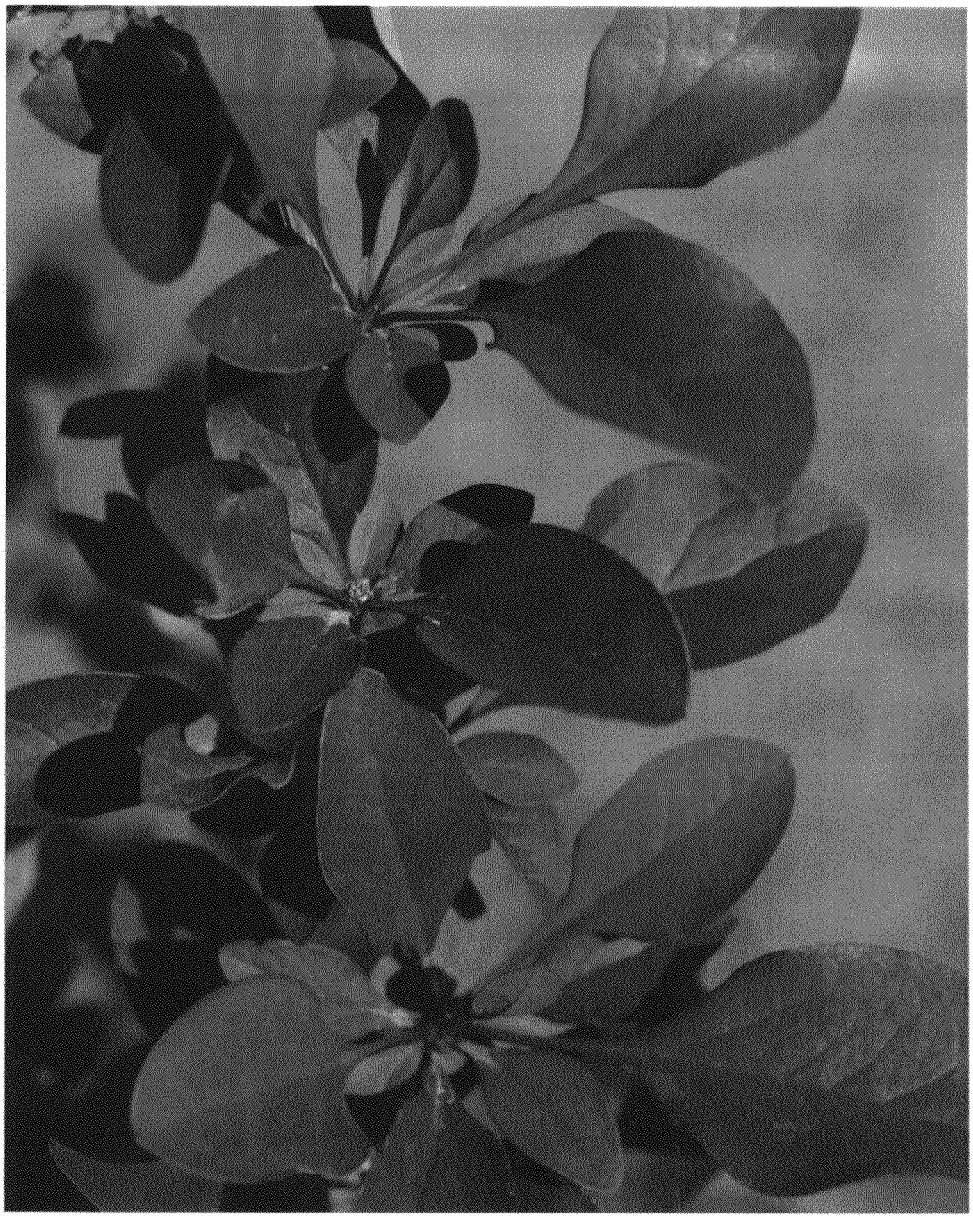

* * * * *